(12) United States Patent
Abovitz et al.

(10) Patent No.: US 7,383,073 B1
(45) Date of Patent: Jun. 3, 2008

(54) DIGITAL MINIMALLY INVASIVE SURGERY SYSTEM

(75) Inventors: Rony A. Abovitz, Hollywood, FL (US); William F. Tapia, Longwood, FL (US); Robert F. Frechette, Fort Lauderdale, FL (US)

(73) Assignee: Z-Kat Inc., Ft. Lauderdale, FL (US)

( * ) Notice: Subject to any disclaimer, the term of this patent is extended or adjusted under 35 U.S.C. 154(b) by 924 days.

(21) Appl. No.: 09/978,599

(22) Filed: Oct. 16, 2001

(51) Int. Cl.
*A61B 5/05* (2006.01)

(52) U.S. Cl. .................. 600/407; 600/407; 600/424; 600/427

(58) Field of Classification Search ............... 600/407, 600/410, 411, 414, 417, 431, 420–427, 437, 600/439
See application file for complete search history.

(56) References Cited

U.S. PATENT DOCUMENTS

| | | | |
|---|---|---|---|
| 4,370,983 A * | 2/1983 | Lichtenstein | 600/301 |
| 4,523,679 A | 6/1985 | Paikoff et al. | 206/370 |
| 4,577,629 A * | 3/1986 | Martinez | 606/171 |
| 4,583,538 A | 4/1986 | Onik et al. | 128/303 |
| 4,943,939 A | 7/1990 | Hoover | 364/555 |
| 4,945,914 A | 8/1990 | Allen | 128/653 |
| 5,094,241 A | 3/1992 | Allen | 128/653.1 |
| 5,138,712 A | 8/1992 | Corbin | 395/700 |
| 5,142,930 A | 9/1992 | Allen et al. | 74/469 |
| 5,517,990 A | 5/1996 | Kalfas et al. | 128/653.1 |
| 5,553,143 A | 9/1996 | Ross et al. | 380/25 |
| 5,554,097 A | 9/1996 | Guy | 600/102 |
| 5,667,478 A | 9/1997 | McFarlin et al. | 600/182 |
| 5,682,886 A | 11/1997 | Delp et al. | 128/653.1 |
| 5,931,303 A | 8/1999 | Salvadori | 206/570 |
| 5,967,982 A | 10/1999 | Barnett | 600/429 |
| 6,007,243 A * | 12/1999 | Ergun et al. | 378/197 |
| 6,021,343 A * | 2/2000 | Foley et al. | 600/429 |
| 6,035,228 A * | 3/2000 | Yanof et al. | 600/429 |
| 6,052,611 A * | 4/2000 | Yanof et al. | 600/429 |
| 6,069,932 A | 5/2000 | Peshkin et al. | 378/42 |
| 6,073,044 A | 6/2000 | Fitzpatrick et al. | 600/426 |
| 6,161,032 A * | 12/2000 | Acker | 600/424 |
| 6,187,018 B1 | 2/2001 | Sanjay-Gopal et al. | 606/130 |
| 6,246,900 B1 | 6/2001 | Cosman et al. | 600/426 |
| 6,285,902 B1 * | 9/2001 | Kienzle et al. | 600/427 |

(Continued)

FOREIGN PATENT DOCUMENTS

EP 0 119 886 9/1984

Primary Examiner—Angela D. Sykes
Assistant Examiner—Jacqueline Cheng
(74) Attorney, Agent, or Firm—Fay Sharpe LLP

(57) ABSTRACT

A software-integrated disposable kit contains a series of sterile packages which hold instrumented surgical tools, surgical accessories, user input computer controlling peripherals (e.g. mouse, keyboard), markers, and a one time use digital medium. When image guided surgery is to be performed, the digital medium is inserted into the computer and the user interface is displayed. The digital medium stores a portion of the software which, in combination with software on the computer, provides all of the software necessary for full user functionality (e.g. display diagnostic image information, tracking surgical instruments, superimposition of surgical tools). At the end of a surgical procedure, the digital medium is deactivated or encrypted and the used surgical tools are then disposed of without reuse. The system allows the user to save relevant information obtained from the surgery (e.g. images, notes) on the digital medium which is encrypted against reuse and archived.

36 Claims, 3 Drawing Sheets

U.S. PATENT DOCUMENTS 6,331,181 B1 * 12/2001 Tierney et al. ............... 606/130
6,332,891 B1 * 12/2001 Himes ........................ 606/169
6,379,302 B1 *  4/2002 Kessman et al. ........... 600/437
6,425,865 B1 *  7/2002 Salcudean et al. .......... 600/437
6,485,413 B1 * 11/2002 Boppart et al. ............. 600/160
2001/0034530 A1 * 10/2001 Malackowski et al. ..... 606/130

* cited by examiner

DIGITAL MINIMALLY INVASIVE SURGERY SYSTEM

BACKGROUND OF THE INVENTION

The present invention relates to the art of image guided surgery. It finds particular application in conjunction with neurosurgical and orthopedic procedures and will be described with particular reference thereto. However, it is to be appreciated that the present invention is equally applicable to a wide range of image guided surgical applications in humans as well as veterinary applications.

Heretofore, images of a region of a patient in which surgery is planned have been made using magnetic resonance imaging systems, computed tomography, or other similar imaging modalities. These techniques generate a substantial amount of data, which is then manipulated through software to provide three-dimensional guidance within the imaged region. Typically, to facilitate diagnoses and treatment through image guidance, this data is manipulated using a computer supplemented with other specialized computer hardware to display selected views during surgery, e.g., orthogonal views, slices, perspective renderings, or the like.

Acquired images used for image guided surgery typically use anatomical reference markers which are commonly imaged with the patient. At the surgical site, acoustic, infrared, video camera, or other tracking technologies are utilized to determine the location of the markers relative to the patient and the surgical site. Additional computer software is provided to register the coordinate system of the markers, hence the patient, with the image(s). Thereafter, the same system is used to monitor the current position of surgical tools instrumented with similar markers, and coordinate their position in physical space with their position in the image(s). In this manner, the current position of the tool or probe relative to obscured portions of the patient's anatomy is readily determined. This facilitates implementing minimally invasive techniques by allowing the surgeon to use the acquired image(s) to see below the visible surface of the patient. For example, the surgeon can use the software's graphic user interface to mark the entry point and proposed trajectory of a pedicle screw on a patient's spine. The marked image(s) can then be used to enable the surgeon to follow the trajectory created below the surface with the instrumented surgical tool to be sure that the screw will not impinge the spinal cord and that it will engage sufficient bone to anchor properly, and the like.

In prior image guided surgery systems, different tools have been used for different portions of the human anatomy. To accommodate the use of different tools, the surgeon typically needs to calibrate the tool to the system. That is, the system needs to know the length, diameter, distances between various portions of the tool and the markers mounted on the tool, relative locations of markers and a tool axis, and the like. Prior image guided surgery systems did not allow use of non-instrumented or standard surgical tools. Also, in prior image guided surgery systems, as new tools are developed or as tools are modified, information about the tools loaded into the system must be reloaded on the entire installed base. Similar reinstallation problems occur when improvements are made to the software.

Prior image guided surgery systems also relied on reusable surgical tools. This has several drawbacks. First, with use, tools with cutting edges become dull. Second, since the tools are sterilized between uses, infection to the patient is possible due to a potential failure of the sterilization procedure.

Typically, image guided surgery systems are universal, i.e., applicable to any portion of the human anatomy that can be clearly imaged with reference markers. Computer software is provided to handle the imaging and alignment needs in virtually any region of the human anatomy. In some instances, the image guided surgery software is incorporated directly into the diagnostic imaging device. In other instances, additional expensive hardware is provided separately.

Prior image guided surgery systems have also relied on a capital equipment sales model, which has resulted in limited market acceptance. Prior image guided surgery systems have been large in size and cost-prohibitive for most. The shipping logistics has been expensive and cumbersome.

The present invention contemplates a new and improved method for image guided surgery, which overcomes the above-referenced problems and several others.

SUMMARY OF THE INVENTION

In accordance with one aspect of the present invention, a method of image guided surgery is provided which includes use of a (1) low cost integrated computer, (2) software-integrated disposable kits, (3) sterile disposable surgical tools and accessories, and a (4) tracking system used to locate the instrumented surgical tools during surgery.

In accordance with another aspect of the present invention, a low cost integrated computer is provided. The computer contains a portion of image guided surgery software to provide minimal user functionality e.g., retrieval of previously saved surgical information, preoperative surgical planning, etc. Image guided surgery using this method is not possible with the computer alone. Full user functionality is enabled only when the proper digital medium obtained from a software-integrated disposable kit, as described below, is inserted into a drive on the computer. Standard peripherals e.g., keyboard, mouse, are also included with kit. A display is also provided but is not part of the kit. Wireless peripherals can also be included as part of the kit to enable remote access to the software's graphic user interface. The computer can be included as part of a low cost mobile cart as well.

In accordance with another aspect of the present invention, a software-integrated disposable kit is also provided which includes (1) sterile instrumented disposable surgical tools and (2) a disposable one-time use digital medium, which contains the remaining a portion of the image guided surgery software to enable full user functionality. The digital medium will contain at least (i) a one-time use application specific software module and (ii) descriptive information concerning the surgical tools and other accessories. Further, other accessories, such as cables used to connect the computer to an imaging device e.g., fluoroscope, in sterile condition in sterile packaging which are used in the identified surgical procedure are present in the kit. Other accessories, including but not limited to implants and other associated hardware may be included depending on the application.

In accordance with another aspect of the present invention, sterile instrumented disposable surgical tools are also provided. The tools are in sterile condition in sterile packaging and are used in the identified surgical procedure. The tools are instrumented with markers that can be visualized during an image guided surgery by a tracking system.

In accordance with another aspect of the present invention, an application specific software module is contained on the digital medium. The software module can only be used once and will function only when used in conjunction with the portion of the image guided surgery software that resides on the computer.

In accordance with another aspect of the present invention, acoustic, infrared, video camera, or other tracking systems are utilized to determine the location of the instrumented surgical tools. The tracking system can be used to track other accessories e.g., a registration phantom, as well. The tracking system can be incorporated into a separate mobile cart or integrated directly into the operating room infrastructure e.g., lights, ceiling.

At a surgical site, the digital medium is removed from the software-integrated disposable kit and inserted into the computer. The software which resides on the computer in conjunction with the software on the digital medium, processes electronic medical diagnostic images, registers the acquired images to the patient's anatomy, registers the acquired images to any other acquired imaging modalities e.g., fluoroscopy to CT, MRI. The location of the instrumented surgical tool(s) is tracked by simultaneously updating the tool's virtual representation in the image(s), or any combination or subset thereof, with movement of the tool(s) in physical space. After the surgery, the digital medium and the surgical tool(s) are disposed of as they are disposable and can only be used once.

One advantage of the present invention resides in low or no capital cost to hospital and medical facilities for the equipment.

Another advantage of the present invention is that it enables automatic upgrade of the image guided surgery software and of the specifications, descriptions, and characteristics of the surgical tools residing on the computer upon insertion of the digital medium.

Yet another advantage of the present invention is the assured sterility of the surgical tools, accessories, and any other components of the system contained in the software-integrated disposable kit, which enter the sterile field.

Another advantage of the present invention is the assured sharpness and reliable maintenance of any other quality aspects of the surgical tools and guides.

Another advantage includes simplified patient billing.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1:
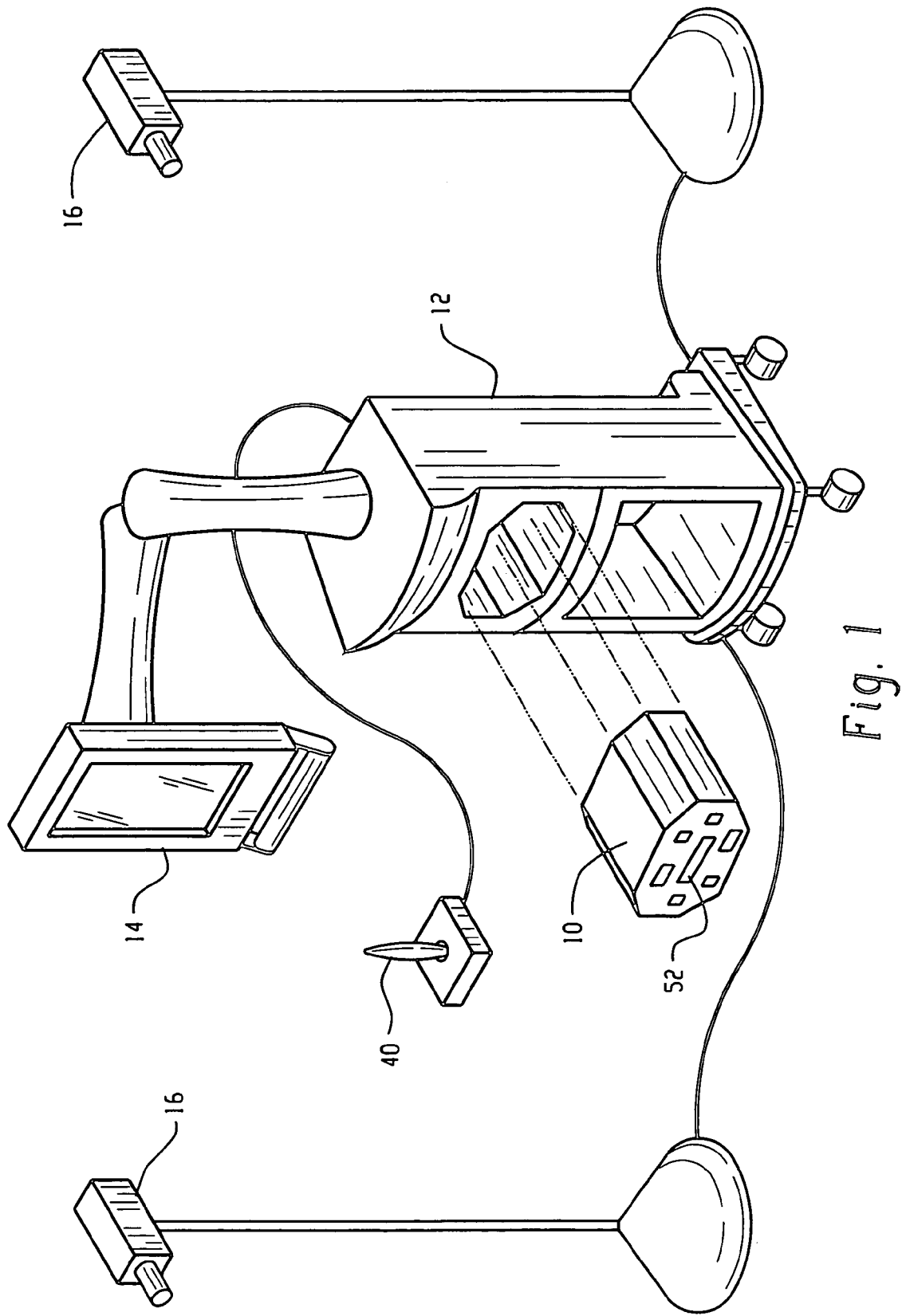
FIG. 1 is a perspective view of a mobile cart in combination with a computer with peripherals including but not limited to a joystick, a display, accessories including but not limited to cables, and a tracking system in accordance with the present invention.

With reference to FIG. 1, one embodiment of the invention mentioned herein includes a computer 10 that is mounted in a mobile cart 12 or other convenient location in a surgical suite outside of the sterile field. This may be on the wall or on a hospital cart that is not in use. In the illustrated embodiment, as the computer 10 is inserted into the cart, a series of electrical interconnections are made, including interconnection with a display e.g., a flat screen monitor 14, interconnection with an electrical wall outlet, backup power supply unit contained within the cart, or some combination thereof, interconnection with one or several tracking system cameras 16, and the like. The tracking system cameras 16 for tracking the location of markers including but not limited to acoustic sensors, infrared sensors, and the like, are mounted on mobile carts, suspended from the ceiling of the surgical suite, mounted in conjunction with other equipment in the surgical suite such as the lighting, the operating table, or the like. In one embodiment, the cart 12 includes a port for connecting the computer 10 with the central record storage system of the hospital via a network, a diagnostic imaging device 64, or other source of electronic images of the patient. In other embodiments, the computer 10 includes a disk, tape, or other media drive for receiving the image information via a portable medium.

Figure 2:
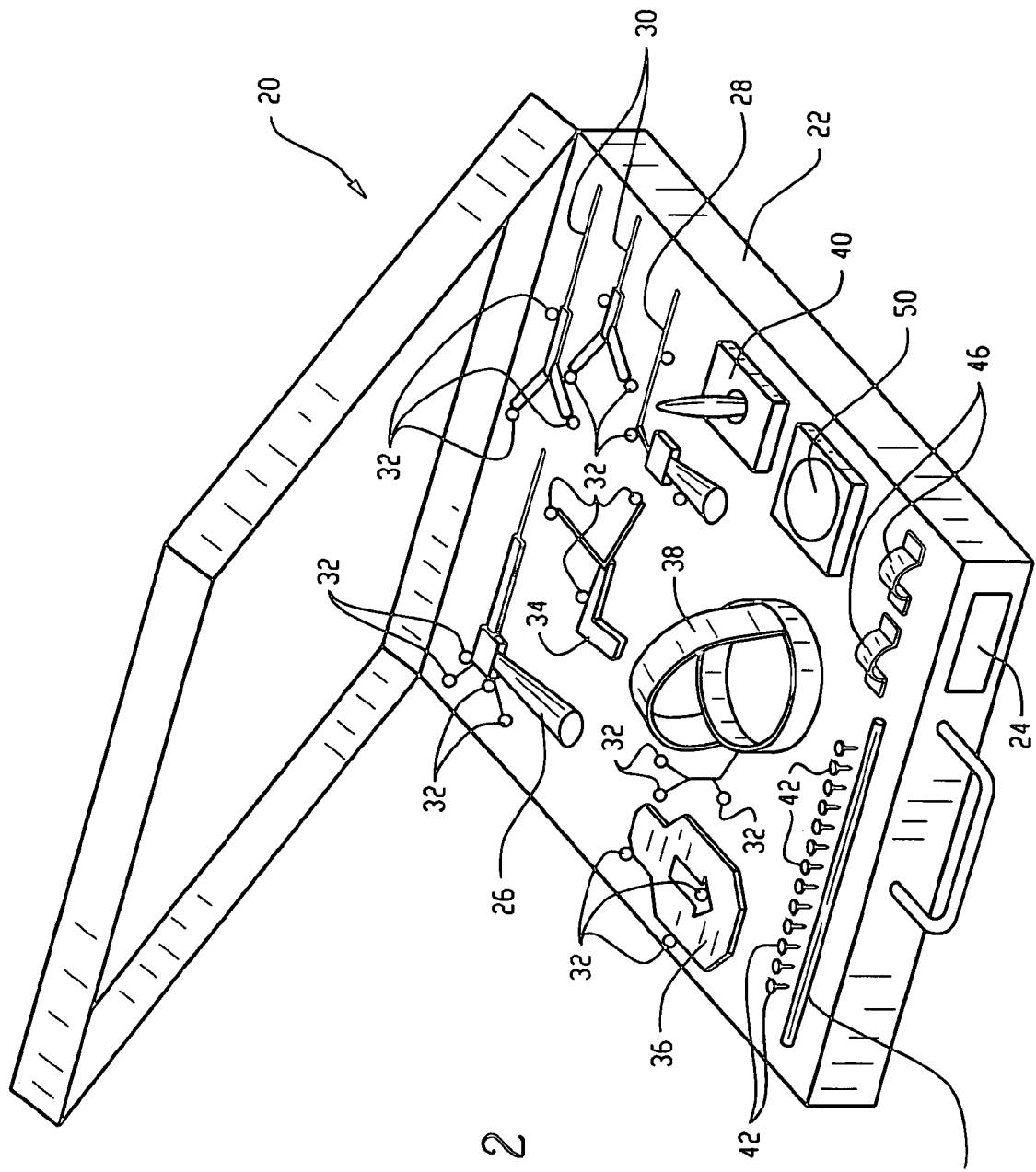
FIG. 2 is a perspective view of a software-integrated disposable kit in accordance with the present invention; and, FIG. 3 is a diagrammatic illustration of a schematic for the computer in accordance with the present invention.

With reference to FIG. 2, for each surgical application, there is a corresponding software-integrated disposable kit 20. The kit 20 includes a sealed, e.g., shrink-wrapped, carry-case or unit 22 which contains all of the necessary equipment for performing a specific surgical procedure indicated on a label 24 on the outside of the kit. A variety of kits 20 are provided, each labeled for a specific surgical procedure or limited group of closely related surgical procedures. Each kit 20 typically includes the appropriate surgical tools for the corresponding procedure, such as instrumented drill guides 26, 28, instrumented probes 30, and other accessories as may be appropriate to the selected procedure. The tools are instrumented with markers 32 which are tracked by the cameras 16, in the preferred embodiment. Additional markers 32 not attached to a tool may be included in the kit 20. In other embodiments, the markers 32 are acoustic or infrared transmitters whose signals are received by corresponding acoustic or infrared cameras 16. By tracking the markers 32 with one or several cameras 16, the current location of each marker 32, hence the associated tool, is readily determined by well-known triangulation techniques. In other embodiments, more than two cameras 16 or other sensors are provided for improved tracking even when the surgeon temporarily blocks access to one of the markers 32. Each of the drill guides 26, 28, probes 30, and other surgical tools and accessories are presterilized and wrapped in peel-open or other sterile packaging.

The kit 20 further includes several other components which are commonly used during image guided surgery. These components can include a universal tool tracker 34 which is mounted directly to a fixed location on the tool. The universal tool tracker 34 is used to track standard surgical tools that are not included as part of the kit 20. A registration phantom 36 that is attached to the operating room table or directly to the imaging device is also included and is used to register an acquired image(s) to the patient's anatomy. Depending on the surgical procedure, other components may be included such as a head frame 38 with markers for attachment to the patient. All the components contained in the kit 20 are again presterilized and prepackaged in sterile packaging.

The kit 20 further includes, but is not limited to, a user input device(s) 40 such as a joystick, mouse or keyboard with which the operator controls the software's graphic user interface. The user input device(s) 40 and their associated cable(s) are sterile and packaged in sterile packaging. During set-up for the procedure, the sterile packaging is opened and the cable(s) for the user input device(s) 40 is plugged into a corresponding port on the computer 10 or mobile cart 12. Another embodiment includes a wireless user input device(s) that is recognized by the system, through an infrared port for example on the computer 10 or mobile cart 12.

The kit 20 can further include implants 42 and other surgical accessories that are used in the selected surgical procedure. For example, the kit 20 can include pedicle screws 42, rods 44, and mounting clamps 46, and the like as are appropriate for a surgical procedure on the spine. Different surgical procedures will, of course, have different surgical accessories in the kit 20. The surgical accessories are sterile and sealed in sterile packaging.

The kit 20 further includes a one-time-use digital medium 50, such as a small high-capacity diskette, CD-ROM, DVD, or the like. The digital medium 50 is configured to be received into a drive 52 in the computer 10. The diskette 50 contains a portion of the software to be used during a surgical procedure, image processing algorithms specific to the application, dimensions and other specifications of the surgical tools and accessories in the kit 20, and other information of use during the surgical procedure.

Figure 3:
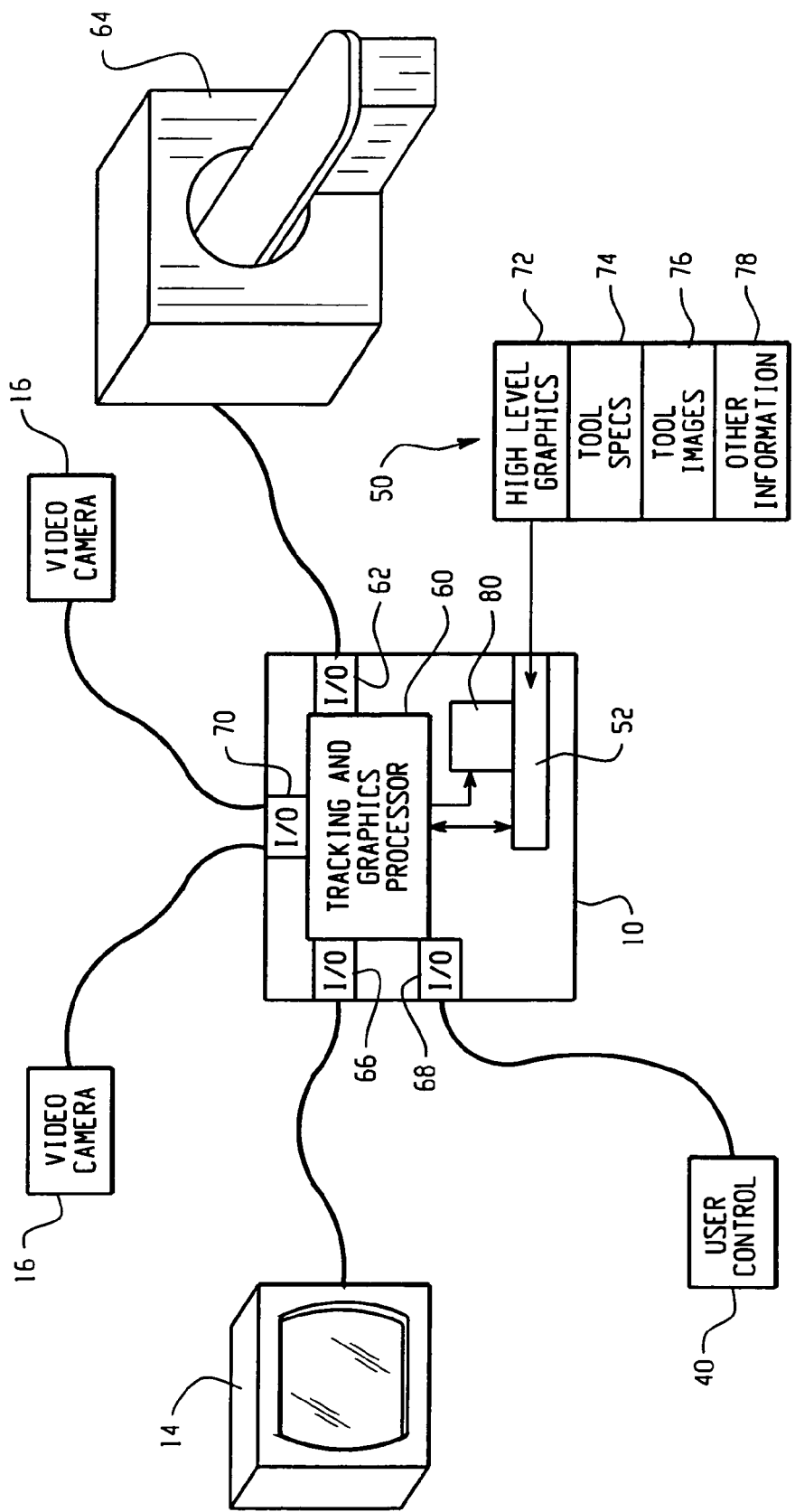

With reference to FIG. 3, the computer 10 may include triangulation or tracking software and base or low-level graphics and other processing software 60. A video-grabber card or other similar input/output device for capturing still-images or live video includes an input/output port and/or interface 62 for receiving electronic images directly from an imaging device 64. Images can also be received through the computer network port by accessing central record keeping via the hospital's network. Optionally, the computer 10 may include a drive for reading the electronic image information obtained from the imaging device 64 from disk, tape, or other similar media. The computer 10 also includes a graphics card or the like with a port and/or interface 66 for connecting to the display 14. Likewise, the computer 10 includes a port and/or interface 68 for interconnection with the user input device 40. The computer 10 may also contain a port, an infrared port for example, for wireless connection to the user input device(s). The computer 10 further includes a port and/or interface assembly 70, which interfaces the tracking system's cameras 16 with the tracking software.

The one-time-use digital medium 50, in the preferred embodiment is a mini-diskette, which includes information useful for a specific surgical application. The medium contains an area for high-level graphics processing software 72 with the most recently revised algorithms for the graphics processes which are specific to the selected surgical procedure. The disks for different surgical procedures may have different high-level graphics processing software and information. The high-level graphics processing software 72 interacts with the low-level graphic processing software 60 to enable the computer 10 to perform the image and graphics processing which it may be called upon to perform during the selected surgical procedure. Various other electronic keys, including media such as CD-ROM and DVD for example, for enabling the computer 10 for image guided surgery are also contemplated.

The digital medium 50 further includes an area 74 for software which describes tool specifications. That is, software to describe the specifications of each of the tools, probes, guides, and any other necessary accessories in the kit. In conjunction with the tool(s) physical specifications, markers 32, and the tracking system's cameras 16, the image guided surgery software recognizes the tool and correlates its position, trajectory, end point, and any other necessary characteristics in physical space with it's virtual representation on the display 14.

The digital medium 50 further includes an area 76 for 3D virtual representations, images, or information, in VRML format for example, of the instrumented tools contained in the kits. These files are used to create 3D virtual representations of each of the surgical tools. The 3D representations of the tools are superimposed on each acquired and registered image. These representations can be in wireframe or fully rendered format, for example, depending on the surgeon's preference. The 3D surgical tool information or image area 76 is accessed by the software on the computer and the digital medium and manipulated so the tools virtual representation in the image(s) is correlated to its 3D position in physical space as determined by the camera(s) 16.

The digital medium 50 further includes an area 78 for software that describes other information such as instructions with guides concerning common steps taken during the surgical procedure. For example, this section may include software information concerning the depth and diameter of the holes to be tapped for the surgical screws in the kit. It may include information or guidelines for the use or placement of the accessories in the kit, images from a previous or similar procedure, anatomy atlas tables containing information on certain anatomical angles and distances specific to an application, and the like. This portion of the digital medium 50 may also include software for upgrading the low-level graphics processing software 60 to the latest released revision.

The invention further includes a means 80 to ensure one-time-use of the digital medium 50. This means preferably resides in the computer 10. In one embodiment, this means erases all or part of the digital medium at the end of the procedure. Alternately, the software is encrypted to block reuse. In another embodiment, the digital medium 50 is physically deformed to prevent reuse. After the procedure, the tools and the digital medium 50 are disposed. Alternatively, the tool and the medium 50 are returned to the company for inspection, remanufacture, cleaning, sterilization, and/or repackaging. Alternatively, the digital medium can also be used to store data obtained during surgery i.e., notes, images, etc. In this case, the digital medium 50 is archived.

In a preferred marketing procedure, the computer 10 is of limited cost. The computer 10 is sold to the hospitals at nominal or no cost. The cost of the computer 10 is recovered by the sale of the single use kits 20, the price of which is gauged to cover the cost of maintaining the computer 10 as well as the tools and accessories. This business model eliminates the traditional capital equipment sale process for conventional image guided surgery equipment. It also facilitates patient billing.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. An image guided surgery system comprising:
   a computer pre-programmed with a portion of image guided surgery software that provides minimal user functionality, full user functionality being enabled by adding application specific software, the computer being disposed at a surgical site;
   a software-integrated disposable kit including:
      an openable, transportable case;
      instrumented surgical tools for a preselected surgical procedure, the tools being removably disposed in the case;
      a digital medium with the application specific software specific to the preselected surgical procedure for upgrading the image guided surgery software to facilitate performance of the preselected surgical procedure, the digital medium being removably disposed in the case;
      the case being openable at the surgical site such that the surgical tools are removable from the case at the surgical site for use in the preselected surgical procedure and the digital medium is removable from the case and insertable in the computer to enable full functionality of the image guided surgery software for the preselected surgical procedure;
   a tracking system which locates the surgical tools while in use, the tracking system being disposed at the surgical site; and
   a display at the surgical site used in conjunction with the computer.

2. The image guided surgery system as set forth in claim 1 further including:
   a low cost mobile cart that holds at least the computer, the display, and standard peripherals.

3. The image guided surgery system as set forth in claim 1 wherein when the computer receives and reads the digital medium, the image guided surgery software is fully functional for the preselected surgical procedure and when the digital medium is removed, the image guided surgery software provides the minimal user functionality.

4. An image guided surgery system including:
   software-integrated disposable kits including:
      a digital medium with application specific software; and,
      instrumented disposable surgical tools;
   a computer which receives the digital medium and processes the application specific software;
   a tracking system which tracks the surgical tools during a surgical procedure;
   a display used in conjunction with the computer; and
   a means for deactivating or encrypting the digital medium against reuse at the end of the surgical procedure.

5. The image guided surgery system as set forth in claim 4 wherein the computer includes:
   an input/output interface for capturing still-images and/or live video from an imaging device;
   a graphic input/output interface for connecting to the display;
   an interface for interconnection with at least one of a wired user input device and a wireless user input; and,
   an interface for interconnection with tracking sensors for monitoring position and movement of the instrumented surgical tools.

6. The image guided surgery system as set forth in claim 4, wherein the digital medium includes:
   preprogrammed software for superimposing instrumented tools, accessories, implants, and associated hardware on images on the display in a wire frame or a user selected custom format.

7. The image guided surgery system as set forth in claim 4 wherein the digital medium includes:
   an area which stores the application specific software;
   an area which stores specifications and characteristics of the instrumented surgical tools;
   an area which stores 3D virtual representations, images, or information of the instrumented tools and accessories contained in the kit; and
   an area which stores additional information relevant to a particular surgical procedure.

8. The image guided surgery system as set forth in claim 4 wherein the tracking system includes:
   one of acoustic sensors, infrared sensors, and video cameras, that are utilized to determine a location of the instrumented surgical tools.

9. The image guided surgery system as set forth in claim 4 wherein the tracking system includes:
   a mobile cart for positioning a tracking camera in a surgical suite.

10. An image guided surgery system comprising:
    an integrated computer;
    a software-integrated, single-use, preselected surgical procedure specific kit including:
       a portable, openable housing;
       a label affixed to the housing to identify the preselected surgical procedure to be performed using the kit;
       sterile packaging in which surgical tools for the preselected surgical procedure are contained in sterile condition, the sterile packaging and tools being removably disposed in the housing;
       other accessories for the preselected surgical procedure in sterile condition in sterile packaging, the other accessories and their sterile packaging being removably disposed in the housing;
       user input devices removably disposed in the housing; and
       a disposable, one-time use digital medium readable by the computer and containing a portion of image guided surgery software specific to the preselected surgical procedure, the digital medium being removably disposed in the housing;
    a tracking system which locates the surgical tools while in use; and,
    a display used in conjunction with the computer.

11. The image guided surgery system as set forth in claim 10 wherein the user input devices include:
    a disposable, sterilizable, wireless peripheral for use by a surgeon at a surgical site for remote communication with the computer.

12. An image guided surgery system comprising:
    a software-integrated disposable kit including:
    instrumented disposable surgical tools;
    a digital medium with application specific software, the digital medium including:
       a preprogrammed one-time-use application specific software module to be used in surgery; and
       a preprogrammed software module describing the surgical tools, implants, and other accessories;
    the instrumented disposable surgical tools and the digital medium being packaged in a common shipping unit from which the tools and digital medium are removable at a surgical site;

a tracking system which tracks the surgical tools during surgery;

a computer which receives the software from the digital medium before a surgical procedure and disables it after the procedure; and, a display used in conjunction with the computer.

13. An image guided surgery system comprising:

a computer;

a software-integrated, one-time-use kit including:
- a shipping case;
- surgical tools removably received in the shipping case; and,
- a digital medium which includes: preprogrammed software describing dimensional specifications of each of the tools, probes, guides, and any other instrumented accessories contained in the kit, the digital medium being removably received in the shipping case; and a tracking system which tracks the surgical tools while in use; and, a display connected with the computer.

14. A surgery system comprising:

an integrated computer;

a display used in conjunction with the computer;

software-integrated kits, each kit designed for a preselected surgical procedure and including:
- a common case;
- surgical tools for performing the preselected surgical procedure;
- a digital medium preprogrammed with software of 3D virtual representations, images, or information regarding the surgical tools, and any accessories, implants, and associated hardware contained in the kit used to create 3D virtual representations of the surgical tools in images on the display;
- the surgical tools and the digital medium both being removably disposed in the common case.

15. A method of image guided surgery using a computer, a one-time-use surgical application specific kit that contains a digital medium with application specific software and surgical tools and accessories, a tracking system that locates the surgical tools while in use, and a display, the method comprising:

at a surgical site in preparation for a surgical procedure, removing the digital medium from the kit and inserting the digital medium into the computer;

augmenting software on the computer with the software from the digital medium to process diagnostic images, register the diagnostic images to a patient's anatomy, register different sets of imaging modalities to each other, and track locations of at least one surgical tool;

during the surgical procedure, displaying a virtual representation of the at least one surgical tool on an image on the display, correlating movement of the virtual representation on the image on the display with movement of the at least one surgical tool in physical space;

deactivating or encrypting the digital medium against reuse after the surgical procedure.

16. The method as set forth in claim 15 further including: using the computer as a planning station before the surgical procedure to define surgical entry points and trajectories.

17. The method as set forth in claim 15 further including: archiving on the digital medium a record or history of the performed surgical procedure, including downloaded diagnostic images, selected instruments, implants, length of surgical time, notes, or other relevant information obtained during the surgical procedure.

18. The method as set forth in claim 15 further including: replaying archived data for review and diagnostic follow-up.

19. The method as set forth in claim 15 further including: preventing reuse of the surgical tools.

20. The method as set forth in claim 15 further including: disposing of the surgical instruments and the digital medium without reuse after the surgical procedure.

21. A method of image guided surgery comprising:

providing a kit which includes (1) instrumented surgical tools and accessories and (2) a digital medium which is preprogrammed with software including (i) at least a portion of a graphics processing program and (ii) information concerning the surgical tools and accessories;

at a surgical site, removing the digital medium from the kit and inserting it into a processor which, between software with which the processor is preprogrammed and the software from the digital medium, processes electronic medical diagnostic images, correlates a coordinate system of a patient with a coordinate system of the diagnostic images, tracks a location of the instrumented surgical tools in the coordinate system of the patient, and translates the instrument position of the surgical tools into the coordinate system of the diagnostic image;

at the surgical site, removing the surgical tools and accessories from the kit.

22. The method as set forth in claim 21 wherein the kit further includes:

medical appliances, and a user control for interconnection with the processor to control image displays; and the method further includes:

at the surgical site, removing the medical appliances and the user control from the kit.

23. The method as set forth in claim 22 further including: prior to placing the surgical tools, the surgical appliances, and the user control in the surgical kit, packaging the surgical tools, the surgical appliances, and user control in sterile condition in sterile packaging.

24. The method as set forth in claim 22 further including: prior to placing the digital medium in the kit, programming the medium, with information about the surgical tools and the medical appliances in the kit.

25. The method as set forth in claim 21 further including: prior to placing the digital medium in the kit, programming the digital medium with dimensional information about and depictions of the surgical tools.

26. The method as set forth in claim 21 further including: after a surgical procedure, deactivating the digital medium against reuse.

27. The method as set forth in claim 26 further including: after the surgical procedure, disposing the surgical instruments and the digital medium without reuse.

28. A surgical kit comprising:

a housing;

an identification of a surgical procedure to be performed using the kit, the identification being attached to an exterior of the housing;

surgical tools in sterile condition in sterile packaging which are used in the identified surgical procedure, the tools being removably received in the housing;

medical appliances in sterile condition in sterile packaging which are used in the identified surgical procedure, the medical appliances in sterile packaging being removably disposed in the housing;

an operator control in sterile condition in sterile packaging for electrical interconnection with a graphics processor which is preprogrammed with image guided surgery software that provides limited user functionality outside a sterile field, the operator control in sterile packaging being removably disposed in the housing; and, a digital media preprogrammed with a portion of an image guided surgery processing program and descriptive information concerning the surgical tools and the appliances in the kit which is readable by the processor to upgrade the preprogrammed image guided surgery software to full user functionality for the identified surgical procedure, the digital media being removably disposed in the housing.

29. An image guided surgery system comprising:

a set of surgical tools which are instrumented to be tracked during image guided surgery;

a processor which is preprogrammed with less than all software which is used for manipulating diagnostic images during the image guided surgery and for tracking the movement of the instrumented surgical tools during the image guided surgery;

a digital media which is preprogrammed with a remaining portion of the software for processing the diagnostic image data and tracking the movement of the instrumented surgical tools and with descriptive information concerning the instrumented surgical tools; and a deactivator which deactivates the digital media against reuse at the end of an image guided surgical procedure.

30. The system as set forth in claim 29 wherein the processor includes:

a reader which receives and reads the digital media.

31. The system as set forth in claim 29 further including a surgical kit which includes:

an indication of a surgical procedure with which the kit is to be utilized;

the instrumented surgical tools for use in the indicated surgical procedure; and, the digital media.

32. The system as set forth in claim 31 wherein the surgical kit further includes:

surgical appliances used in the indicated procedure; and a user input control for controlling the processor, the user input control, the surgical appliances, and the surgical tools all being in sterile condition in the kit.

33. The system as set forth in claim 29 wherein the processor includes:

an interface for interconnection with a source of three-dimensional electronic diagnostic images;

an interface for interconnection with a human-readable display for displaying diagnostic images and superimposed representations of the surgical tools;

an interface for interconnection with a user input control; and, an interface for interconnection with optical sensors for monitoring position and movement of the instrumented surgical tools.

34. The system as set forth in claim 29 wherein the digital media includes:

a first memory portion which stores the remaining software portion;

a second memory portion which stores descriptive characteristics of the instrumented surgical tools;

a third memory section which stores shape displays corresponding to the surgical tools for display superimposed on a display of the diagnostic image; and, a fourth memory portion which carries additional information.

35. An image guided surgery system having a tracking system for tracking movement of surgical tools, a human-viewable display, and a computer with limited user functionality for retrieving surgical information, displaying and manipulating diagnostic images on the display, surgical planning, and superimposing representations of the surgical tools on the diagnostic images on the display, further including:

a single use digital medium containing software to upgrade the computer temporarily to full user functionality for a preselected surgical procedure; and, a means for disabling the software from being reused to upgrade the computer after the preselected surgical procedure.

36. A method of implementing a computer-implemented procedure, the method comprising:

providing an integrated computer which receives a digital medium and which renders the digital medium inoperative;

opening a software-integrated disposable kit and removing a digital medium with application specific software and any associated elements;

inserting the digital medium into the integrated computer;

performing the procedure;

deactivating or encrypting the digital medium against reuse in the integrated computer;

removing the digital medium from the integrated computer.

* * * * *